US010343150B2

(12) United States Patent
Minoux et al.

(10) Patent No.: US 10,343,150 B2
(45) Date of Patent: Jul. 9, 2019

(54) PROCESS FOR PREPARING A MESOPORIZED CATALYST, CATALYST THUS OBTAINED AND USE THEREOF IN A CATALYTIC PROCESS

(71) Applicant: TOTAL RAFFINAGE FRANCE, Courbevoie (FR)

(72) Inventors: Delphine Minoux, Nivelles (BE); Nadiya Danilina, Uccle (BE)

(73) Assignee: TOTAL RAFFINAGE FRANCE, Courbevoie (FR)

( * ) Notice: Subject to any disclaimer, the term of this patent is extended or adjusted under 35 U.S.C. 154(b) by 322 days.

(21) Appl. No.: 14/347,159

(22) PCT Filed: Oct. 24, 2012

(86) PCT No.: PCT/EP2012/071017
§ 371 (c)(1),
(2) Date: Mar. 25, 2014

(87) PCT Pub. No.: WO2013/060705
PCT Pub. Date: May 2, 2013

(65) Prior Publication Data
US 2014/0249344 A1    Sep. 4, 2014

(30) Foreign Application Priority Data

Oct. 24, 2011 (FR) ................................. 11 59618
Dec. 29, 2011 (FR) ................................. 11 62520

(51) Int. Cl.
*B01J 29/12* (2006.01)
*B01J 37/06* (2006.01)
(Continued)

(52) U.S. Cl.
CPC ............ *B01J 29/126* (2013.01); *B01J 29/06* (2013.01); *B01J 29/068* (2013.01); *B01J 29/072* (2013.01);
(Continued)

(58) Field of Classification Search
CPC ........ B01J 29/126; B01J 29/084; B01J 29/06; B01J 29/068; B01J 29/072; B01J 29/076;
(Continued)

(56) References Cited

U.S. PATENT DOCUMENTS 3,293,192 A    12/1966 Maher et al.
3,506,400 A    4/1970 Eberly et al.
(Continued)

FOREIGN PATENT DOCUMENTS

EP    0 082 211 A1    6/1983
EP    0 519 573 A1    12/1992
(Continued)

OTHER PUBLICATIONS

Krijn et al (NPL: "Zeolite Y Crystals with Trimodal Porosity as Ideal Hydrocracking Catalyst" Angewandte Chemie (International ED, in English), vol. 122, No. 52, Dec. 27, 2010, pp. 10272-10276 and supporting information).*
(Continued)

*Primary Examiner* — Melvin C. Mayes
*Assistant Examiner* — Smita S Patel
(74) *Attorney, Agent, or Firm* — Sughrue Mion, PLLC

(57) ABSTRACT

The invention relates to a process for preparing a catalyst comprising a mesoporized zeolite, comprising the steps of: preparation of a protonic mesoporized zeolite, which contains at least one network of micropores and at least one network of mesopores, and
treatment in a gas or liquid phase containing ammonia or ammonium ions.

(Continued)

The invention also related to the obtained catalyst and the use of this catalyst in hydroconversion processes.

15 Claims, 4 Drawing Sheets

(51) Int. Cl.

| | |
|---|---|
| *B01J 38/08* | (2006.01) |
| *B01J 29/06* | (2006.01) |
| *B01J 29/068* | (2006.01) |
| *B01J 29/072* | (2006.01) |
| *B01J 29/076* | (2006.01) |
| *B01J 29/08* | (2006.01) |
| *B01J 29/14* | (2006.01) |
| *B01J 29/16* | (2006.01) |
| *B01J 35/00* | (2006.01) |
| *B01J 35/10* | (2006.01) |
| *C01B 39/02* | (2006.01) |
| *C01B 39/06* | (2006.01) |
| *C01B 39/24* | (2006.01) |
| *C10G 49/08* | (2006.01) |
| *B01J 29/90* | (2006.01) |
| *C07C 4/06* | (2006.01) |

(52) U.S. Cl.
CPC ............ *B01J 29/076* (2013.01); *B01J 29/084* (2013.01); *B01J 29/146* (2013.01); *B01J 29/166* (2013.01); *B01J 29/90* (2013.01); *B01J 35/002* (2013.01); *B01J 35/108* (2013.01); *B01J 35/109* (2013.01); *B01J 35/1095* (2013.01); *B01J 37/06* (2013.01); *B01J 38/08* (2013.01); *C01B 39/026* (2013.01); *C01B 39/06* (2013.01); *C01B 39/24* (2013.01); *C07C 4/06* (2013.01); *C10G 49/08* (2013.01); *B01J 2229/14* (2013.01); *B01J 2229/16* (2013.01); *B01J 2229/186* (2013.01); *B01J 2229/22* (2013.01); *B01J 2229/36* (2013.01); *B01J 2229/37* (2013.01); *B01J 2229/38* (2013.01); *B01J 2229/42* (2013.01); *C07C 2529/068* (2013.01); *Y02P 20/584* (2015.11)

(58) Field of Classification Search
CPC ........ B01J 29/146; B01J 29/166; B01J 29/90; B01J 29/12; B01J 29/08; B01J 35/002; B01J 35/108; B01J 35/109; B01J 35/1095; B01J 2229/14; B01J 2229/16; B01J 2229/186; B01J 2229/22; B01J 2229/36; B01J 2229/37; B01J 2229/38; B01J 2229/42; B01J 37/06; C01B 39/026; C01B 39/06; C01B 39/24; C10G 49/08; C07C 4/06
See application file for complete search history.

(56) References Cited

U.S. PATENT DOCUMENTS

| | | | |
|---|---|---|---|
| 3,929,672 A | 12/1975 | Ward | |
| 4,093,560 A | 6/1978 | Kerr et al. | |
| 5,069,890 A | 12/1991 | Dai et al. | |
| 5,207,892 A | 5/1993 | Vassilakis et al. | |
| 5,601,798 A | 2/1997 | Cooper et al. | |
| 5,952,535 A * | 9/1999 | King | B01J 29/18 208/138 |
| 2012/0018349 A1 | 1/2012 | Van Donk et al. | |

FOREIGN PATENT DOCUMENTS

| | | |
|---|---|---|
| EP | 0 528 494 A1 | 2/1993 |
| WO | 95/07236 A1 | 3/1995 |
| WO | 2010/072976 A1 | 7/2010 |
| WO | WO 2010072976 A1 * | 7/2010 ............ B01J 29/084 |

OTHER PUBLICATIONS

Bourgeat-Lami et al (NPL: "study of the state of aluminum in zeolite-Beta", Applied catalysis, 72, 1991 pp. 139-152).*
Donk et al., Generation, Characterization, and Impact of Mesopores in Zeolite Catalysts, Catalysts Reviews 45 (2003), pp. 297-319.
Janssen et al., Three-Dimensional Transmission Electron Microscopic Observations of Mesopores in Dealuminated Zeolite Y, Angew. Chem. Int. Ed. 40 (2001), pp. 1102-1104.
Ogura et al., Formation of Uniform Mesopores in ZSM-5 Zeolite through Treatment in Alkaline Solution, Chem. Lett. (2000), pp. 882-883.
Ogura et al., Alkali-treatment technique—new method for modifcation of structural and acid-catalytic properties of ZSM-5 zeolites, Appl. Catal. A Gen. 219 (2001), pp. 33-43.
Groen et al., On the inroduction of intracrystalline mesoporosity in zeolites upon desilication in alakline medium, Microporous Mesoporous Mater. 69 (2004), pp. 29-34.
Groen et al., Optimal Aluminum-Assisted Mesoporosity Development in MFI Zeolies by Desilication, J. Phys. Chem. B, 108 (2004), pp. 13062-13065.
Katada et al., Dealumination of proton form mordenite with high aluminum content in atmosphere, Micropor. Mesopor. Mater. 75 (2004), pp. 61-67.
E. Bourgeat-Lami et al., Study of the state of aluminum in zeolite-B, Appl. Catal. 72 (1991), pp. 139-150.
Woolery, et al., On the nature of framework Bronsted and Lewis acid sites in ZSM-5, Zeolites 19 (1997) 288-296.
Omegna et al., Flexible Aluminum Coordination in Alumino-Silicates, Structure of Zeolite H-USY and Amorphous Silica—Alumina, J. Phys. Chem. B. 107 (2003), pp. 8854-8860.
Wouters et al., Reversible Tetrahedral-Octahedral Framework Aluminum Transformation in Zeolite Y, J. Am. Chem. Soc. 120 (1998), pp. 11419-11425.
Xu et al., Reversibility of structural collapse in zeolite Y: Alkane cracking and characterization, J. Catal. 241 (2006), pp. 66-73.
Bokhoven et al., Three-Coordinate Aluminum in Zeolites Observed with In situ X-ray Absorption Near-Edge Spectroscopy at the Al K-Edge: Flexibility of Aluminum Coordinations in Zeolites, J.Am. Chem. Soc. 125 (2003), pp. 7435-7442.
Krijn P. De Jong et al., "Zeolite Y Crystals with Trimodal Porosity as Ideal Hydrocracking Catalysts," Angew. Chem. 2010, p. 10272-10276, vol. 122, No. 52; additional Supporting Information from Angew. Chem. attcahed.
Bin Xu et al., "Effect of framework Si/Al ratio and extra-framework aluminum on the catalytic activity of Y zeolite," Applied Catalysts A: General, 2007, pp. 245-253, vol. 333, No. 2.
S. Altwasser et al., "Elucidating the Dealumination Mechanism of Zeolite H-Y by Solid-State NMR Spectroscopy," Studies in Surface Science and Catalysts, Elsevier B.V, vol. 154 (2004), pp. 1-8, XP-002675557 (ISR designation).
International Search Report of PCT/EP2012/071017 dated Jul. 3, 2013.

* cited by examiner

PROCESS FOR PREPARING A MESOPORIZED CATALYST, CATALYST THUS OBTAINED AND USE THEREOF IN A CATALYTIC PROCESS

CROSS REFERENCE TO RELATED APPLICATIONS

This is a National Stage of International Application No. PCT/EP2012/071017 filed Oct. 24, 2012, claiming priority based on French Patent Application No. 11 59618 filed Oct. 24, 2011 and French Patent Application No. 11 62520 filed Dec. 29, 2011, the contents of all of which are incorporated herein by reference in their entirety.

The invention relates to a process for preparing a mesopores-containing catalyst, the catalyst thus obtained and the use of the catalyst thus obtained in an industrial process.

The catalyst described here comprises a mesoporized zeolite and may be used in many hydroconversion processes, in particular, in the hydrocracking process.

PRIOR ART

The various zeolites are distinguished by different structures and properties, and are well known in the art. A few structures commonly used in the field of catalysis are disclosed in WO2010/072976, among them some are given below.

Zeolite Y (FAU) is a three-dimensional zeolite with large pores, whose structure has large cavities interconnected by channels formed from 12-membered rings, each ring presenting 12 ($Si^{4+}$ and $Al^{3+}$) cations and 12 $O^{2-}$ anions.

Beta zeolite (BEA) is a three-dimensional zeolite with large pores comprising pores formed from 12-membered rings in all directions.

Zeolite ZMS-5 (MFI) is a virtually three-dimensional zeolite with medium-sized pores, comprising pores formed from 10-membered rings in one direction that are interconnected by zig-zag channels formed from 10-membered rings (this is why this structure is considered as being virtually three-dimensional).

Mordenite (MOR) is a zeolite with large pores formed from 12-membered rings, with channels extending in only one direction and which has between these channels small pockets formed from 8-membered rings.

Ferrierite (FER) is a two-dimensional zeolite with medium-sized pores comprising main channels formed from 10-membered rings, which are interconnected via side channels formed from 8-membered rings.

Zeolites are important catalytic materials and widely used in acid-catalyzed reactions such as cracking (e.g. hydrocracking, FCC, olefin cracking), isomerization reactions (e.g. of paraffins and olefins) and more recently, methanol conversion technologies (e.g. MTO, MTP, MTG). For all these reactions, the zeolite is the heart of the catalyst, rendering high catalytic activity, high stability, and last but not least high product selectivity, induced by the microporous zeolite structure. Notwithstanding the positive effect of the presence of micropores with respect to shape selectivity, the micropores may also have a negative impact, which is often illustrated by the low rate of access of molecules into the zeolite crystals, or unwanted adsorption effects of reactants and/or products during the catalytic action. These steric constraints decrease the accessibility of the zeolite micropore volume during the catalytic action, and it can be stated that the zeolite crystals are not always being used effectively.

One of the important issues in the development of new zeolite catalysts is the guarantee of sufficient accessibility of the active sites for reactant and/or product molecules, thereby maximizing the effectiveness of the catalyst. The straightforward solution to minimize diffusion limitation would be the reduction of the intracrystalline diffusion pathlength. One possibility is to decrease the zeolite crystal size. Another strategy, to obtain materials with sufficient accessibility is the creation of a secondary pore system consisting of mesopores (2-50 nm) inside the microporous zeolite crystals. Traditionally, mesopores are introduced into zeolites and zeolite-like crystals by dealumination, using hydrothermal treatment such as steaming [U.S. Pat. Nos. 3,293,192, 3,506,400, and 5,069,890], and acid leaching techniques [U.S. Pat. Nos. 3,506,400, 4,093,560, and 5,601, 798]. Alternatively, chemical treatments, with for example EDTA [U.S. Pat. Nos. 3,506,400 and 4,093,560] or $(NH_4)_2SiF_6$ [EP0082211], have been proposed as well. A more detailed literature review on the generation of mesopores in zeolites by various methods, was presented by van Donk et al. [S. van Donk et al., Catalysis Reviews 45 (2003) 297].

Despite of the considerable developments over the last years in the domains of the synthesis, characterization and comprehension of the formation mechanisms of these structured mesoporous materials, their effective application in industry is still highly limited because of their high cost, which is partially related to the high cost of the organic template. Therefore, from a cost perspective, the classical hydrorthermal and acid leaching techniques remain highly attractive, which explains why they are largely used today in industry. However, the introduction of mesopores by these ways is not easily controlled and often materials are obtained with a random and non-optimized mesoporosity. In a paper by Janssen et al. [A. H. Janssen et al., Angew. Chem. Int. Ed. 40 (2001) 1102], it was demonstrated using three-dimensional electron microscopy that a large part of the mesopores in a commercially available steamed and acid-leached zeolite Y (CBV780, Zeolyst Int.) were cavities, not optimally connected to the outer surface of the zeolite crystal. Obviously, for catalysis, a system of interconnected cylindrical mesopores is expected to enhance the accessibility for reactants and the diffusion of reaction products much more than mesoporous cavities inside the crystal.

In recent years, as an alternative to the classical hydrorthermal and acid leaching of the as-synthesized zeolite material, another approach for the formation of mesopores has been proposed [M. Ogura et al., Chem. Lett. (2000) 82; M. Ogura, Appl. Catal. A Gen. 219 (2001) 33; J. C. Groen et al., Microporous Mesoporous Mater. 69 (2004) 29; J. C. Groen, et al., J. Phys. Chem. B, 108 (2004) 13062]. This alternative method is based on the careful desilication of the as-synthesized zeolite by a treatment in an alkaline medium. This technique was firstly explored in the late 1980's for studying dissolution phenomena and structural changes in zeolite Y and ZSM-5. Furthermore, two patents were assigned to Shell on the modification of ultra-stable and very ultra-stable Y-zeolites with a Si/Al ratio between 2 and 12.5 at/at [EP0528494] and their application in a hydrogenation process [EP0519573].

Recently, the Applicant has disclosed in the patent application WO 2010/072 976 a modified zeolite Y prepared by careful desilication of a dealuminated faujasite, resulting in a material which had a unique trimodal system of intracrystalline and interconnected pores. This zeolite showed an improved performance in several hydrocracking reactions, being more selective to middle distillates and suppressing overcracking. Middle distillates comprise a range of products from the middle boiling fraction of the crude oil barrel.

Hydrocracking reactions are gaining on importance with the need to treat heavier and more polluted feedstocks and with an increasing demand for middle distillates in Europe. Therefore, a middle distillates-selective hydrocracking catalyst is seeked.

However, often the activity of mesoporous catalysts synthesized by the destructive techniques is significantly lower compared to the catalysts based on the purely microporous zeolites. The improvement in diffusivity of the mesoporous zeolites is often reached by the loss of long-range crystallinity, microporosity, amount of framework aluminum and the closely associated amount of Brønsted acid sites. These characteristics are often responsible for the activity of the catalyst, particularly, in acid-catalyzed reactions. The change in aluminum coordination alters the number of Brønsted acid sites in the catalyst, which is directly related to the catalytic activity [N. Katada et al., Micropor. Mesopor. Mater. 75 (2004) 61].

In zeolite beta, octahedrally coordinated aluminum forms and can be converted to tetrahedral aluminum by adsorption of basic molecules, such as ammonia, as well as by substitution of the protons by sodium and potassium cations [E. Bourgeat-Lami et al., Appl. Catal. 72 (1991) 139]. The presence of aluminum species that reversibly convert coordination on ammonia adsorption was also found in the zeolites ZSM-5 [G. L. Woolery et al., Zeolites 19 (1997) 288], MOR [A. Omegna et al., J. Phys. Chem. B. 107 (2003) 8854] and Y [B. H. Wouters et al., J. Am. Chem. Soc. 120 (1998) 11419; B. Xu et al., J. Catal. 241 (2006) 66]. Similar behavior was observed in amorphous silica aluminas [A. Omegna et al., J. Phys. Chem. B. 107 (2003) 8854]. In acidic zeolites, the transformation of the coordination of aluminum from tetrahedral to octahedral occurs at room temperature after contact with moisture; at temperatures above 400 K, octahedral coordination is unstable [J. A. van Bokhoven et al., J. Am. Chem. Soc. 125 (2003) 7435] and reverts back to tetrahedral coordination, although the Brønsted acid site is not restored [A. Omegna et al., J. Phys. Chem. B. 107 (2003) 8854].

Therefore, to combine the diffusional advantages of the mesoporous structure with the preserved zeolitic properties, a post-synthesis treatment after the introduction of mesopores should be considered. Such a post-synthesis treatment could help healing the partially destroyed zeolite structure by re-inserting the extra-framework aluminum into framework positions.

DESCRIPTION OF THE INVENTION

The Applicant has now discovered a process for preparing a catalyst comprising a mesoporized zeolite showing good catalytic activity, especially in hydroconversion reactions, due to the so-called "healing" of the zeolitic structure by a post-synthesis treatment of a mesoporized material.

According to a first aspect, a subject of the invention is a process for preparation of a catalyst comprising a mesoporized zeolite, including the steps of:
A—preparation of a protonic mesoporized zeolite, which contains at least one network of micropores and at least one network of mesopores, and
B—treatment in a gas or liquid phase containing ammonia or ammonium ions.

According to this process, in step B, the partially destroyed zeolite structure after step A) is restored by re-inserting the extra-framework aluminum, i.e generally admitted as being Al atoms in octahedral coordination, into framework positions, i.e also generally admitted as being Al atoms in tetrahedral coordination. Besides, the ratio of the octahedral aluminium to tetrahedral aluminium can be from 0 to 0.5, especially, from 0 to 0.4 and more particularly, from 0 to 0.3. These effects lead to improved catalytic activity, especially when these materials are used in hydroconversion reactions.

The process according to the invention, especially after step B), is thus advantageously consisting of re-inserting the extra-framework aluminum into framework positions of said catalyst.

The process allows the preparation of a catalyst comprising a mesoporized zeolite with healed zeolitic structure, which could also be named in the present specification as "final mesoporized zeolite catalyst". In some embodiments, the catalyst as such is consisting of a mesoporized zeolite with healed zeolitic structure.

The final mesoporized zeolite catalyst obtained after step B) has the following characteristics:
crystallinity of 0 to 100%, preferably from 0 to 98%, for example, from 0 to 95%; higher compared to the material prepared in step A)
specific surface area (BET) from 100 to 850 $m^2/g$, for example, from 150 to 800 $m^2/g$,
external specific surface area from 20 to 500 $m^2/g$, for example, from 30 to 400 $m^2/g$,
total pore volume from 0.2 to 0.9 ml/g, for example, from 0.25 to 0.6 ml/g,
microporous volume in the range of 0.01 to 0.5 mL/g, especially, 0.002 to 0.4 mL/g,
mesoporous volume (pores between 2 and 50 nm) between 0.1 and 0.9 mL/g, especially, between 0.12 and 0.8 mL/g,
amount of octahedrally coordinated Al lower compared to that in the material prepared in step A)
atomic Si/Al ratio in the zeolite framework between 7 and 40, for example, between 8 and 40,
amount of Brønsted acid sites: from 0.1 to 0.6 mmol $NH_3$/g, for example, from 0.15 to 0.5 mmol $NH_3$/g; higher compared to the material prepared in step A).

In some aspects, the zeolite or a composite material comprising it as starting material used in step A) preferably presents a framework atomic Si/Al ratio between 10 and 50.

Advantageously, the starting material is a zeolite of a FAU framework type and is, in some aspects, a zeolite Y.

In summary, a zeolite of a certain or predetermined framework atomic Si/Al ratio has been mesoporized by base treatment bringing with it a partial destruction of the zeolitic structure (step A)). Upon the above-described $NH_3$-treatment or with ammonium ions (step B)), the zeolitic part of the material has been healed due to the re-insertion of extra-framework Al into the framework positions; whereas the mesoporosity remained preserved. A mesoporized zeolite with healed zeolitic structure has been prepared. The combination of mesoporosity and healed zeolitic structure can lead to an optimal combination of selectivity to middle distillates and high activity in numerous reactions.

Thus the process according to the invention in particular includes a treatment of a zeolite, as starting material, having a predetermined framework atomic Si/Al ratio, in a basic pH medium (step A)) and a treatment of the protonic mesoporized zeolite obtained in step A) in a gas or liquid phase containing ammonia or ammonium ions.

Step A)

A protonic mesoporized zeolite is a zeolite having protons as counter ions.

Step A) of preparation of the protonic mesoporized zeolite may include the following steps:

a) suspending a parent zeolite as starting material or a composite material comprising it in a basic aqueous solution comprising at least one strong base, especially NaOH or KOH, and/or an inorganic or organic weak base, such as sodium carbonate, sodium citrate or a tetraalkyl ammonium hydroxide, for example, at a concentration ranging from 0.001 to 2 M, at room temperature, with magnetic or mechanical stirring,
b) neutralizing the medium by addition of at least one acid, for example, at a concentration ranging from 0.005 to 2 M, at room temperature, with stirring,
c) separating the zeolite obtained from the liquid and optionally washing it with a solvent, especially a polar solvent, for example, water,
d) optionally drying the washed zeolite,
e) optionally performing at least one ion exchange treatment of the zeolite from step c) or of the optionally dried zeolite from step d),
f) optionally washing the zeolite,
g) calcining the zeolite obtained, and
h) recovering the zeolite, i.e the protonic mesoporized zeolite.

The non limitative step a) includes a treatment of a parent zeolite by suspension thereof in a basic solution. The parent zeolite may also be a composite material comprising it, especially at a content of at least 5% by weight relative to the total weight of the composite material.

A composite material is a material containing a certain fraction of a parent zeolite, but also optionally an amorphous phase produced during the modification of the parent zeolite and/or a binder being a metal oxide or a mixture of metal oxides. The zeolite used during step a) of the process preferably presents a bulk atomic Si/Al ratio of greater than or equal to 12.

A zeolite of such atomic framework Si/Al ratio may be also obtained, for example, after at least one dealumination treatment, in particular, a partial dealumination treatment, for example, with at least one acid and/or water vapour. These treatments may lead to (i) reduction in the acidity of the material, (ii) increase, albeit slightly, in the mesoporosity of the initial material, which is theoretically purely microporous. Most particularly, these treatments correspond to those described in U.S. Pat. No. 5,601,798.

In step a), the basic pH solution/zeolite weight ratio may range from 4 to 100, or even from 20 to 100, preferably from 5 to 80, especially from 30 to 80, in particular, from 40 to 60, or may even be about 50.

The base concentration of the solution in step a) may range from 0.001 to 2 M, especially, from 0.005 to 1, in particular, from 0.01 to 0.5, or may even be about 0.05 M.

In step a), the placing in contact with a basic solution may last from 5 to 120 minutes, especially, from 10 to 60 minutes and in particular, from 15 to 30 minutes. During this placing in contact, the suspension may be stirred, especially, by magnetic or mechanical stirring.

The neutralization according to step b) may be performed by contacting with an acid-containing solution, for example, sulphuric acid under industrial conditions, on a large amount of material. The neutralization step may likewise be performed in presence of water. This neutralization is advantageously carried out at room temperature under magnetic or mechanical stirring.

The acid-containing solution is comprising at least one acid, for example, at a concentration ranging from 0.005 to 2 M, at room temperature, under stirring.

The purpose of the neutralization is to stop the desilication process and to prevent the undesired destruction of the material that can result in extensive loss of crystalline structure of the zeolite, loss of microporosity and induce a decrease in the intrinsic activity of the material.

The process also includes, after the step b), a step c) of separating the mesoporized zeolite from the neutralized solution by any known means to obtain a solid mesoporized zeolite, followed by the washing step.

The mesoporized zeolite may then be dried (step d)). The drying step may be performed at a temperature greater than or equal to 70° C., especially, greater than or equal to 75° C., or even greater than or equal to 80° C. It may range from 1 to 36 hours, especially, from 1 to 24 hours and in particular, from 1 to 15 hours. The drying may be performed in air or under an inert atmosphere.

The drying step may last until the weight of the product no longer changes, in particular, when the difference between the weight of the product at a time t and the weight of this product after two hours of heating changes by less than 0.1% by weight relative to the total weight of the product.

The step e) may include placing the washed (step c)) or optionally dried (step d)) zeolite in contact with a solution containing ammonium ions in order to perform the at least one ion exchange treatment.

The ion exchange solution, advantageously comprising a solution containing ammonium ions, especially $NH_4NO_3$, and the mesoporized zeolite weight ratio, may range from 3 to 75, especially from 3 to 50, in particular, from 3 to 30. The $NH_4NO_3$ concentration of the solution of step e) may range from 0.01 to 0.5 M, especially, from 0.05 to 0.4, in particular, from 0.1 to 0.3, or may even be about 0.2 M.

Placing in contact with the solution containing ammonium ions (step e)) may last from 1 to 24 hours, especially, from 1 to 12 hours, in particular, from 1 to 8 hours. This step may be performed one to three times.

Advantageously, step e) can be carried out at room temperature, therefore, do not require heating.

For the purposes of the present invention, the term "room temperature" means a temperature ranging from 10 to 55° C. and in particular, between 15 and 35° C.

The washing step f) may in some aspects be optional, and if so may be carried out with water.

The calcination step (step g)) may be performed at a temperature of greater than or equal to 400° C., especially, greater than or equal to 450° C., or even greater than or equal to 500° C. The heating may last from 1 to 8 hours, in particular, from 1 to 6 hours, or even from 1 to 5 hours. The heating may comprise a temperature rise of 0.5 to 2° C./minute and especially, 1° C./minute. The heating may be performed in air or under an inert atmosphere.

Then, the catalyst essentially consisting of a protonic mesoporized zeolite is recovered (step h)).

By implementing step A) of the process a protonic mesoporized zeolite catalyst can be obtained exhibiting a trimodal porosity, represented by at least one network of micropores and at least one network of mesopores, the latter advantageously including at least one network of small mesopores with a mean diameter of 2 to 5 nm and at least one network of large mesopores with a mean diameter of 10 to 50 nm, these various networks being interconnected.

The protonic mesoporized zeolite of the present invention thus can have trimodal intracrystalline porosity, i.e. containing three networks of pores of different mean diameters within each crystal.

More specifically, the protonic mesoporized zeolite presents a micropore volume that is 10%, especially, 20%, in particular, 30%, or even 50% less than the micropore volume of the starting zeolite.

The protonic mesoporized zeolite may have a mesopore volume that is 10%, especially 20%, in particular 30%, or even 55% higher than the mesopore volume of the starting zeolite. In particular, the increase in mesopore volume is essentially due to the creation of small mesopores.

The protonic mesoporized zeolite may have an atomic bulk Si/Al ratio of less than or equal to 50, especially, less than or equal to 40, or even less than or equal to 30, more particularly, less than or equal to 25, even more particularly, less than or equal to 23 and optionally, less than or equal to 20.

The bulk Si/Al atomic ratio may be greater than or equal to 5, especially, greater than or equal to 6, or even greater than or equal to 7.

The atomic framework Si/Al ratio may lay between 7 and 40.

The protonic mesoporized zeolite advantageously has a ratio of the volume of the small mesopores (Vs) to the volume of the large mesopores Vl, Vs/Vl, of greater than or equal to 1, especially greater than or equal to 1.20, or even greater than or equal to 1.60, more particularly, greater than or equal 1.80 and even more particularly, greater than or equal to 2.

The protonic mesoporized zeolite has a total mesopore volume of greater than or equal to 0.20 ml/g, especially greater than or equal to 0.25 ml/g, in particular, greater than or equal to 0.35 ml/g, or even greater than or equal to 0.40 ml/g.

The protonic mesoporized zeolite has a micropore volume of less than or equal to 0.20 ml/g, especially, less than or equal to 0.18 ml/g, in particular, less than or equal to 0.16 ml/g, or even less than or equal to 0.125 ml/g and more particularly, less than or equal to 0.10 ml/g.

The zeolite prepared according to step A) has a total mesopore volume/micropore volume ratio of greater than or equal to 1, especially, greater than or equal to 1.5, in particular, greater than or equal to 3, or even greater than or equal to 3.5, more particularly, greater than or equal to 4, even more particularly, greater than or equal to 4.5 or even greater than or equal to 5.

The protonic mesoporized zeolite may have an external surface area $S_{ext}$ of greater than or equal to 100 m$^2$/g, especially, greater than or equal to 150 m$^2$/g, in particular, greater than or equal to 200 m$^2$/g, or even greater than or equal to 250 m$^2$/g and more particularly, greater than or equal to 300 m$^2$/g.

The acid site density, measured by TPD of ammonia (TPD NH$_3$), may be less than or equal to 0.5 mmol/g, especially, less than or equal to 0.48 mmol/g, in particular, less than or equal to 0.45 mmol/g or even less than or equal to 0.4 mmol/g.

Optionally, after performing step A) and before performing step B), a step of treatment with water vapour, preferably at a temperature ranging from 250 to 450° C. for 1 to 6 hours, is performed. This so-called "steaming step" may help to repair/hydrolyse the bonds with aluminium that may have been broken during the alkaline treatment.

Optionally, instead or/and after the steaming step, the material is contacted with an aqueous acid solution of a concentration between 0.01 and 1 M at room temperature, for 5 to 60 minutes under mechanical or magnetic stirring.
Step B)

In step B), the protonic mesoporized material obtained in step A) is subjected to a treatment in a gas or liquid phase containing ammonia or ammonium ions.

The treatment in the gas phase can be carried out by subjecting the optionally steamed protonic mesoporized zeolite obtained in step A) to a treatment with a compound able to release gaseous ammonia (in situ) or ammonium ions. The treatment in a gas or in a liquid phase containing a source of ammonia and/or ammonium ions may thus be performed.

This compound or a mixture of compounds can be pure or diluted with an inert gas, such as nitrogen, helium or argon. The volume percentage of the ammonia/ammonium ions-releasing compound or the ammonia/ammonium ions source can be between 1 and 50 vol %, especially, between, 3 and 40 vol % and particularly, between 5 and 30 vol %. The treatment of step B) can take place in the temperature range between 15 and 600° C., preferentially, 20 and 350° C.

Optionally, the protonic mesoporized and optionally steamed zeolite, could be dried and then calcined in situ prior to the treatment, at temperatures up to 650° C. in oxidative atmosphere, such as oxygen, air, nitrous gases, or/and inert atmosphere, such as nitrogen, helium or argon.

The treatment can take place in the temperature range between 15 and 600° C., especially, between 20 and 350° C., particularly, between 20 and 300° C. The duration of the treatment can be 30 minutes to 24 hours, especially, 1 to 5 hours.

Optionally, a calcination step can be placed before, at temperatures up to 650° C., preferentially, up to 550° C., with a heating rate of 0.1 to 5° C./min, in oxidative atmosphere, such as oxygen, air, nitrous gases, or/and inert atmosphere, such as nitrogen, helium or argon, inert atmosphere being preferred. The calcination may last from 30 minutes to 12 hours, preferentially, 1 to 5 hours.

As a source of ammonia, every N-containing molecule that decomposes to ammonia or forms it can be used. Among them, ammonium salts, ammonium hydroxide, amines, nitrates, nitrites, nitride ligands, carbamides, nitrides, cyanamides, carbamates, amides, carbodiimides, (poly)aminoacids, (poly)iminoacids, (poly)aminoacid salts, (poly)imino acid salts, (poly)amino carboxylates, (poly)imino carboxylates or their mixture.

The treatment in the liquid phase can be carried out by subjecting the optionally steamed protonic mesoporized zeolite obtained in step A) to a treatment in an aqueous solution containing a compound able to dissociate to ammonium ions or to form those. This compound or a mixture of compounds can be for example, among them, ammonium salts, ammonium hydroxide, amines, nitrates, nitrites, nitride ligands, carbamides, nitrides, cyanamides, carbamates, amides, carbodiimides, (poly)aminoacids, (poly)iminoacids, (poly)aminoacid salts, (poly)imino acid salts, (poly)amino carboxylates, (poly)imino carboxylates or their mixture. The weight percentage of the ammonium-releasing compound can be between 1 and 80 wt %, especially, between, 3 and 70 wt % and particularly, between 5 and 60 wt %. The treatment can take place in the temperature range between 10 and 150° C., preferentially, 15 and 120° C., most likely, between 20 and 100° C. The duration of the treatment can be 10 minutes to 24 hours, especially, 30 minutes to 7 hours. The treatment can be carried out several times, one to three times, under mechanical or magnetic stirring, optionally under reflux.

Preferably, in the treatment in the liquid phase a solvent may optionally be used, and during the treatment in the gas phase a pure compound or a compound diluted with an inert gas may be used.

Optionally, the modified zeolite could be dried and then calcined in situ prior to the treatment, at temperatures up to 650° C. with a heating rate of 0.1 to 5° C./min, in oxidative atmosphere, such as oxygen, air, nitrous gases, or/and inert atmosphere, such as nitrogen, helium or argon.

The final mesoporized zeolite catalyst of step B) has the following characteristics:
- crystallinity of 0 to 100%, preferably from 0 to 98%, for example, from 0 to 95%; higher compared to the material prepared in step A),
- specific surface area (BET) from 100 to 850 m²/g, for example, from 150 to 800 m²/g,
- external specific surface area from 20 to 500 m²/g, for example, from 30 to 400 m²/g,
- total pore volume from 0.2 to 0.9 ml/g, for example, from 0.25 to 0.6 ml/g,
- microporous volume in the range of 0.01 to 0.5 mL/g, especially, 0.02 to 0.4 mL/g,
- mesoporous volume (pores between 2 and 50 nm) between 0.1 and 0.9 mL/g, especially, between 0.12 and 0.8 mL/g,
- amount of octahedrally coordinated Al lower compared to that in the material prepared in step A),
- atomic Si/Al ratio in the zeolite framework between 7 and 40, for example, between 8 and 40,
- amount of Brønsted acid sites: from 0.1 to 0.6 mmol $NH_3$/g, for example, from 0.15 to 0.5 mmol $NH_3$/g; higher compared to the material prepared in step A).

The final mesoporized zeolite catalyst, thus containing at least one network of micropores and at least one network of mesopores, exhibits an atomic framework Si/Al ratio of greater than or equal to 2.3, especially, greater than or equal to 3, more particularly, greater than or equal to 6, advantageously of between 7 and 40, for example, between 8 and 40. Said final mesoporized zeolite catalyst is very advantageously a hydroconversion catalyst.

The final mesoporized zeolite catalyst contains less extra-framework aluminum than the zeolite prepared during the step A), i.e the protonic mesoporized zeolite or a mesoporized zeolite with no healed zeolitic structure. Typically the content being reduced by at least 5%, advantageously, by at least 10%, more preferably, by at least 20%, in particular, the extra-framework aluminum content being below 5%, whereas the extra-framework aluminum is represented by octahedrally coordinated species and is characterized by the peak around 0 ppm in the $^{27}Al$ MAS NMR spectrum. For the sample prepared during step B), the ratio of the octahedral aluminum to tetrahedral can be from 0 to 0.5, especially from 0 to 0.4 and more particularly, from 0 to 0.3.

The final mesoporized zeolite prepared during step B) advantageously has a volume of micropores in the range of or 0.01 to 0.5 mL/g, especially, 0.02 to 0.4 mL/g.

The mesopore volume (pores between 2 and 50 nm) lays between or 0.1 and 0.9 mL/g, especially, between 0.12 and 0.8 mL/g.

The process may advantageously include an extrusion step and/or a modification step of the final mesoporized zeolite catalyst (step B)) or of the protonic mesoporized zeolite with metals (step A)).

The obtained modified zeolite may be extruded before or after step B) and modified with metals according to known methods, preferably by impregnation. The metals are advantageously catalytic metals preferably chosen from compounds of group VIII, group VIB and mixture thereof. The previous step(s) may be followed by a calcination step. Group VIB corresponds to group 6 of IUPAC periodic table of the elements (version of Jun. 22, 2007) and comprises Cr, Mo and W. Group VIII (VIIIB) corresponds to groups 8, 9 and 10 of IUPAC periodic table of the elements (version of Jun. 22, 2007) and comprises Fe, Ru, Os, Co, Rh, Ir, Ni, Pd, Pt.

During the extrusion, the binder(s) used may be chosen from the group consisting of alumina, silica, titania, silica-alumina, magnesia and mixtures of one or more of these compounds.

The impregnation may be performed by incipient wetness impregnation or ion exchange. Typically, the active metal precursor is dissolved in an aqueous or organic solution. The solution thus obtained is then added to the modified zeolite, the volume of the solution added being identical or higher than the pore volume of the modified zeolite.

The incipient wetness impregnation may be performed by using various solvents, preferably water, at temperatures from 10 to 100° C.

As an option, the introduction of the catalytic metal(s) may be performed by ion exchange, generally by known methods in the art. However, this specific impregnation method is the preferred implementation owing to its easy implementation and in some instances giving good sought effects.

Among the catalytic metals, platinum, palladium, nickel, cobalt, tungsten or molybdenum, but also other transition metals, can be used, provided they are soluble in above-mentioned medium.

Advantageously, the catalyst contains from 0.1% to 10% by weight of a metal from group VIII, for example, nickel and/or cobalt and/or platinum, and from 1% to 25% by weight of a metal from group VIB, for example, molybdenum.

The extrusion step and modification step with catalytic metals is mainly applied after step B), however, it can be also applied after step A) and before the step B), as previously mentioned.

According to some embodiments, the extrusion step is applied after the step A) using the protonic mesoporized zeolite and before step B), followed by the step B) and then by a subsequent modification step with metals, said metals being chosen from compounds of group VIII, from group VIB and mixture thereof, generally followed by a calcination step. The modification step is preferably an impregnation step, as previously mentioned.

Another aspect of the invention concerns a process for the hydroconversion of hydrocarbon feedstock, for example, hydrocracking or hydroisomerization, in which the feedstock to be treated is placed in contact with a catalyst according to the invention, for example, prepared according to the process of the invention.

The hydrocarbon feedstock is advantageously chosen from the group of light cycle oil, atmospheric distillates, vacuum distillates such as vacuum gasoil, feeds from aromatic extraction units, from solvent dewaxing of base lubricating oils, distillates derived from processes of desulphurisation, deasphalted oils, vegetable or animal oils, oils issued from algae or from bacteria, alone or in mixture. This feedstock may also include squalane.

Particularly, another aspect of the invention concerns a use of the catalyst obtained according to this invention in a hydrocracking process.

Characterization Methods

The methods used to perform the measurements of the various characteristics are generally the standard techniques. More particularly, the following techniques were used in the context of this invention:
i) the chemical composition, in particular, the bulk Si/Al atomic ratio and the Pt content, was determined by X-ray fluorescence spectroscopy;
ii) the structure of the zeolite was defined by X-ray diffraction (XRD). XRD was conducted on a Bruker D8 Discover diffractometer in the range between 5 to 70° with a Cu $K_{\alpha 1}$ radiation using a step-size of 0.02° and time/step of 1 s. The relative crystallinity of the samples was determined by background subtraction method;
iii) the nitrogen adsorption and desorption measurements were performed at the temperature of liquid nitrogen on a Micromeritics Tristar 3000 machine. Before each measurement, the samples were degassed under nitrogen at 300° C. for 840 minutes. The textural properties, defined by the external surface area ($S_{ext}$), the micropore volume ($V_{micro}$) and the mesopore volume ($V_{meso}$), were identified by volumetry with nitrogen using adsorption isotherms recorded at 77 K by applying the state-of-the-art methods [Barett, E. P.; Joyner, L. G.; Halenda, P. P. *J. Am. Chem. Soc.* 1951, 73, 373-380. Rouquerol, F.; Rouquerol, J.; Sing, K. *Adsorption by powders and porous solids*; Academic Press: San Diego, 1999]. The BET method [S. Brunauer, P. H. Emmett and E. Teller, *J. Am. Chem. Soc.*, 1938, 60, 309] was used to calculate the specific surface area. The external specific surface area and the specific pore volume were determined by the t-plot method, an empirical semi-quantitative method based on the comparison of the isotherm adsorption data of a porous sample and a non-porous sample of identical chemical composition and surface nature [K. S. W. Sing, Chem. and Ind., (1968) 1520]; the statistical thickness was calculated by means of the Harkins-Jura formula. The t-plot method is based on the comparison of the isotherm adsorption data for a porous sample and for a non-porous sample of identical chemical composition and surface nature;
iv) the $^{27}$Al and $^{29}$Si MAS NMR spectra were acquired on a 500 MHz Bruker Avance spectrometer A500 equipped with an MAS probe-head of 4 mm. The rotation speed was 15000 Hz. The coordination of the Al and Si species was determined from the spectra. The $^{29}$Si MAS NMR spectra were deconvoluted in order to calculate the atomic Si/Al ratio in the framework of the zeolite;
v) the acidity of the catalysts was established by programmed thermo-desorption of ammonia (TPD $NH_3$) between 100 and 650° C. [Niwa, M.; Iwamoto, M.; Segawa, K. B. *Chem. Soc. Jpn.* 1986, 59] by monitoring the desorbed ammonia by conductivity;
vi) the shape and the size of the crystals as well as the porosity within particular crystals were characterized by transmission electron microscopy and scanning electron microscopy.

DESCRIPTION OF THE FIGURES

The invention is now described with reference to the attached non-limiting drawings, in which.

EXAMPLES

Figure 1:
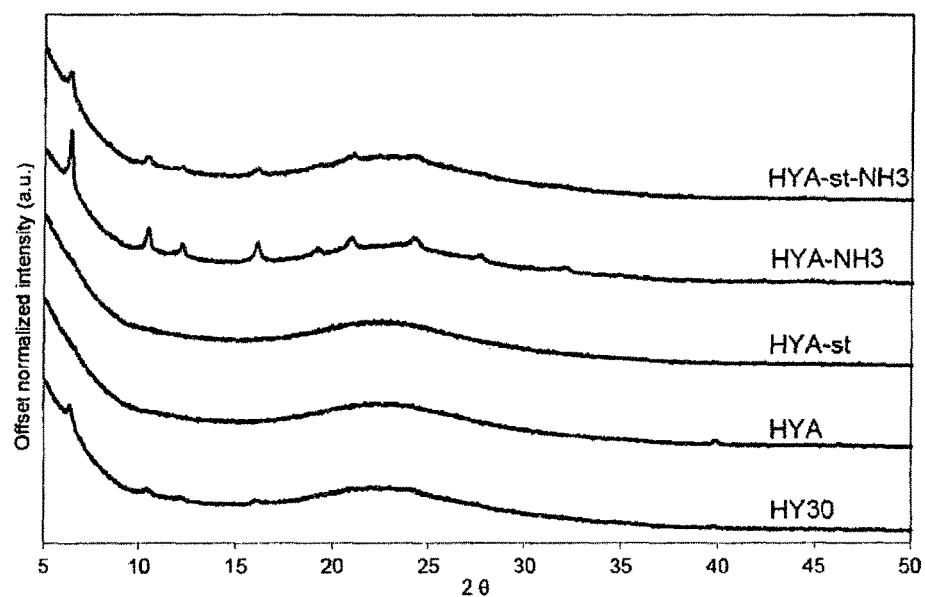
FIG. 1 represents the X-ray diffractograms of the Pt-exchanged zeolite Y (HY30, CBV760, Zeolyst Int.), of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

The zeolite Y (CBV760, Zeolyst Int.) is referred to as HY30.

The characteristics of HY30 are given in Table 2 and graphically represented in FIGS. 1 to 5.

Example 1

Preparation of a Mesoporized Zeolite Y (HYA) and its Steaming (HYA-st)

The compound HY30 is subjected to the following alkaline treatment:
HY30 (200 g) is placed in contact with an aqueous 0.05 M NaOH solution (2500 ml) for 15 minutes at room temperature and under stirring,
the resulting product is filtered off and washed with water,
the filtered product is dried for 12 hours at 80° C.,
aqueous 0.20 M $NH_4NO_3$ solution (2500 ml) is added to the dry product, and the whole is left for 5 hours at room temperature under stirring. This manipulation is performed trice.
the product obtained is washed with water,
the product is then calcined at 500° C. for 4 hours (temperature gradient of 1° C./minute) in a stream of air, and then
the HYA is recovered.

HYA-st is prepared by steaming HYA at 300° C. for 4 hours (temperature gradient 5° C./min).

The characteristics of the samples are given in Table 2, graphically represented in FIGS. 1-5 and discussed in Examples 3 and 4.

Example 2

Treatment of a Mesoporized Zeolite Y before and after Steaming (HYA/HYA-st) with Gaseous $NH_3$ (HYA-NH3/HYA-st-NH3)

HYA and HYA-st are respectively subjected to the following treatment:

The sample (2 g) is placed in a U-formed glass tube and calcined at 550° C. (1° C/min) for 6 hours in a flow of He, Then, the sample is cooled down to 150° C. in a flow of He and stabilized for 30 minutes, The gas is switched from pure He to 10 vol % $NH_3$ in He, The samples are cooled to the room temperature and stabilized for 30 minutes in a flow of 10 vol % $NH_3$ in He, HYA-$NH_3$ and HYA-st-$NH_3$ are respectively recovered.

The characteristics of the samples are given in Tables 1 and 2, graphically represented in FIGS. 1-5 and discussed in Examples 3 and 4.

Example 3

Characterization of the Compounds HYA-st and HYA-st-NH3 before Impregnation with Pt Table 1 summarizes several characteristics of the HYA-st and HYA-st-NH3. The framework atomic Si/Al is decreasing after $NH_3$-treatment, pointing to the re-insertion of some extra-framework Al into the framework positions. The distribution of different Al species shows that mostly pentahedral Al is transformed to tetrahedral framework Al upon $NH_3$-treatment. The re-insertion of Al into the framework positions can be associated with the healing of the structure of zeolite Y.

In summary, a dealuminated zeolite Y has been further mesoporized by base treatment bringing with it a partial destruction of the zeolitic structure. Upon the above-described $NH_3$-treatment, the zeolitic part of the material has been healed due to the re-insertion of extra-framework Al into the framework positions; whereas the mesoporosity remained preserved. A mesoporized zeolite Y with healed zeolitic structure has been prepared. The combination of mesoporosity and healed zeolitic structure can lead to an optimal combination of selectivity to middle distillates and high activity in numerous reactions.

TABLE 1

Summary of the characterization results of HYA-st and HYA-st-NH3

| Sample | | HYA-st | HYA-st-NH3 |
|---|---|---|---|
| Si/Al frame[a] | | 21.87 | 14.62 |
| Al(tetrahedral)[b] | % | 46.7 | 89 |
| Al(pentahedral)[b] | % | 48.7 | 2.9 |
| Al(octahedral)[b] | % | 4.6 | 8.1 |

[a]Si/Al atomic in the framework of the zeolite;
[b]from the deconvolution of $^{27}$Al MAS NMR spectra Example 4

Characterization of the Compounds HY30, HYA, HYA-st, HYA-NH3 and HYA-st-NH3 Ion-exchanged with Pt for Further Catalytic Testing X-ray Diffraction FIG. 1 shows the X-ray diffractograms of the Pt-exchanged zeolite Y (HY30, CBV760, Zeolyst Int.), of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

HYA shows very weak reflections around 6.1, 9.97, 11.69, and 15.39 degrees 2θ, corresponding to the reflections of the FAU structure. The reflections are weak and broad, probably, due to the small crystal size of the sample. There are no visible reflections in the diffractogram of HYA-st. After treatment with gaseous ammonia, the FAU-typical reflections appear in the diffractograms of HYA-NH3 and HYA-st-NH3, indicating the healing of the long-range zeolite structure. The crystallinity increases for the $NH_3$-treated samples (Table 2).

TABLE 2

Summary of the characterization results of Pt-modified HY30, HYA, HYA-st, HYA-NH3 and HYA-st-NH3

| Sample | | HY30 | HYA | HYA-st | HYA-NH3 | HYA-st-NH3 |
|---|---|---|---|---|---|---|
| Crystallinity | % | 8 | 0 | 0 | 21 | 10 |
| Si/Al bulk | | n.d.[g] | n.d. | n.d. | n.d. | n.d. |
| Si/Al frame[a] | | 12.4 | 10.9 | 10.5 | 9.2 | 8.3 |
| $S_{BET}$[b] | m$^2$/g | 296 | 299 | 285 | 467 | 385 |
| $S_{ext}$[c] | m$^2$/g | 296 | 299 | 285 | 325 | 310 |
| $V_{tot}$[d] | ml/g | 0.36 | 0.38 | 0.38 | 0.44 | 0.41 |
| $V_{micr}$[e] | ml/g | 0.01 | 0.01 | 0.01 | 0.07 | 0.04 |
| $V_{meso}$[f] | ml/g | 0.22 | 0.23 | 0.23 | 0.32 | 0.27 |
| TPD-NH3 | mmol/g | 0.36 | 0.33 | 0.38 | 0.46 | 0.38 |
| Pt content | wt % | n.d. | n.d. | n.d. | n.d. | n.d. |

[a]Si/Al in the framework of the zeolite;
[b]BET surface area;
[c]external surface area;
[d]total pore volume;
[e]microporous volume;
[f]mesoporous volume;
[g]not determined.

Nitrogen Sorption

The BET surface areas of the samples HY30, HYA and HYA-st are laying between 285 and 300 m$^2$/g. After the $NH_3$-treatment, the BET surface areas of the corresponding samples are increasing, resulting in 467 m$^2$/g for HYA-NH3 and 385 m$^2$/g for HYA-st-NH3. For the samples before the ammonia-treatment, the BET surface area is corresponding to the external surface area, pointing to the absence of micropores in the samples. After the ammonia-treatment, the microporous volume increases from 0 to 0.07 mL/g for HYA-NH3 and 0.04 mL/g for HYA-st-NH3.

Figure 2:
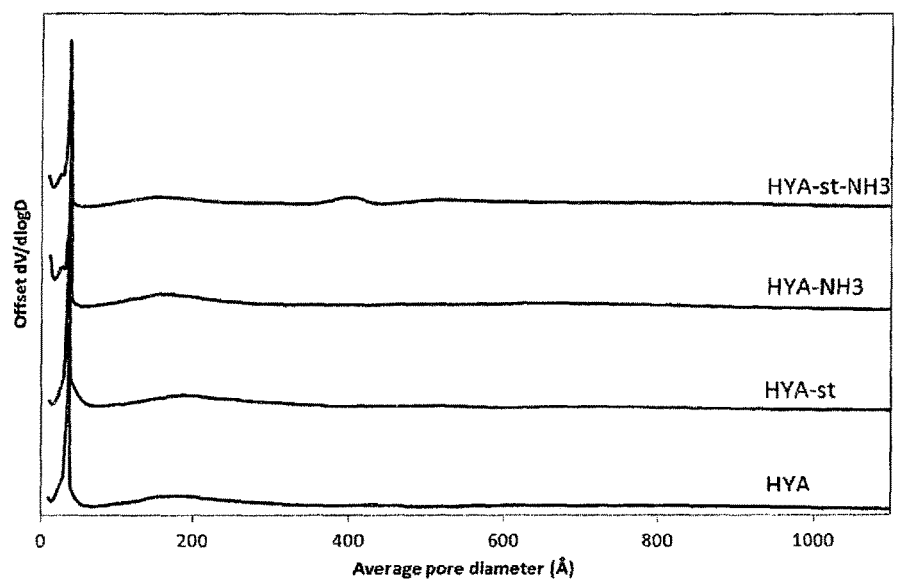
FIG. 2 shows the pore size distribution for the Pt-exchanged zeolite Y (HY30, CBV760, Zeolyst Int.), of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

The mesoporous volume as well as the total pore volume is increasing after the ammonia-treatment, reaching 0.32 mL/g for HYA-NH3. FIG. 2 shows the pore size distribution of HYA, HYA-st, HYA-NH3 and HYA-st-NH3. All catalysts show two maxima in the mesopore region. HYA and HYA-st have maxima around 3 nm and 19 nm, whereas the ammonia-treated samples around 3.1 nm and 16 nm. Therefore, they have at least trimodal porosity taking into account the presence of micropores in these samples.

Elemental Analysis $^{27}$Al MAS NMR Spectroscopy

Figure 3:
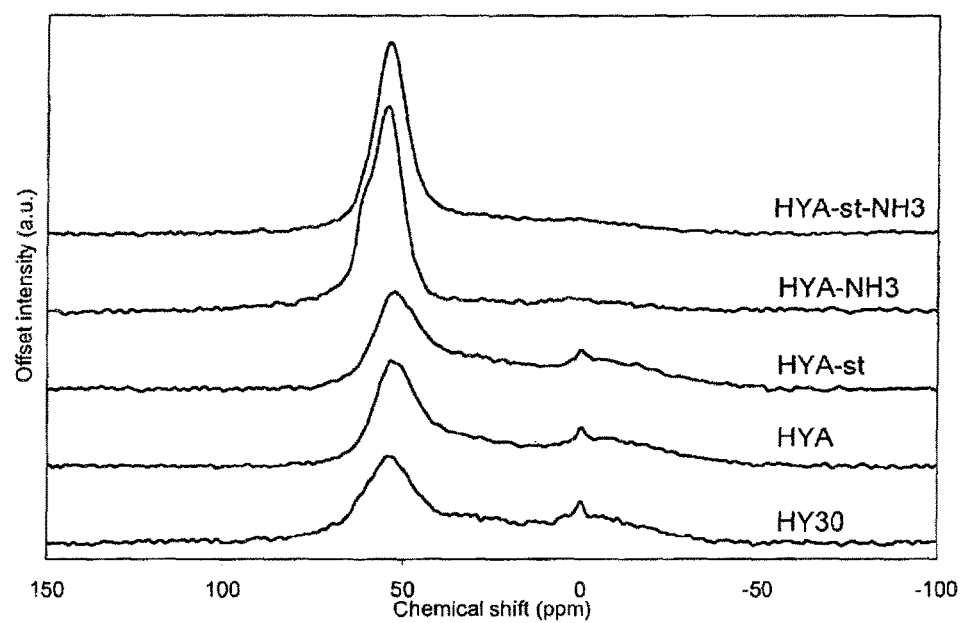
FIG. 3 shows the $^{27}$Al MAS NMR spectra of the Pt-exchanged zeolite Y (HY30, CBV760, Zeolyst Int.), of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

FIG. 3 shows the $^{27}$Al MAS NMR spectra of the Pt-exchanged HY30, of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

All samples show an intense peak at about 55 ppm, corresponding to the tetrahedrally coordinated Al species. HY30, HYA, and HYA-st contain a small amount of octahedrally coordinated Al, represented by the peak at about 0 ppm. After the treatment with ammonia, the octahedrally coordinated Al disappears, whereas the peaks at 55 ppm become more pronounced. As no washing steps were carried out during the treatment with ammonia, we assume that the octahedrally and pentahedrally coordinated Al was reinserted into the framework positions of the zeolite upon treatment with ammonia.

$^{29}$Si MAS NMR Spectroscopy

Figure 4:
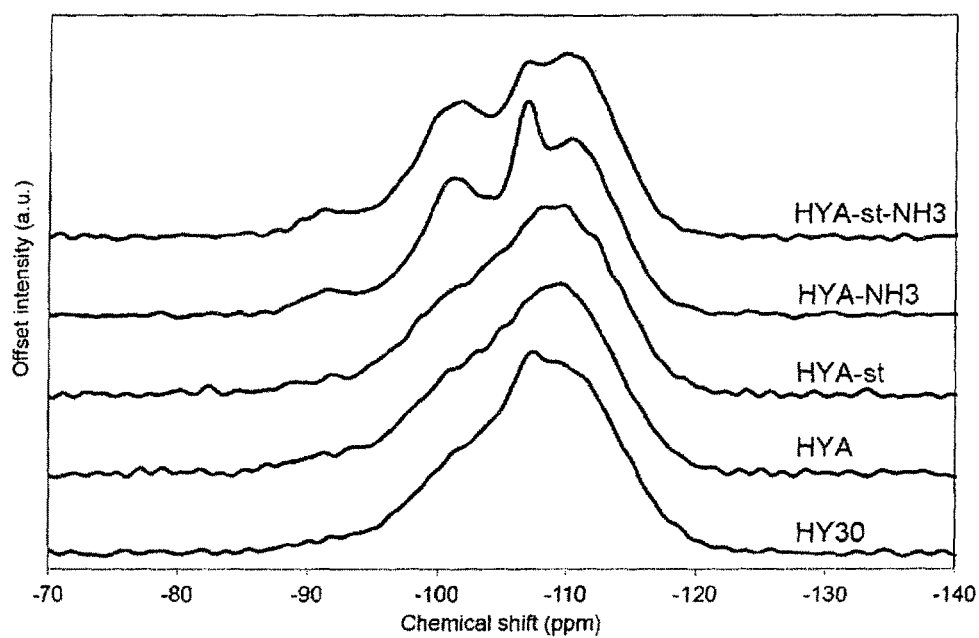
FIG. 4 shows the $^{29}$Si MAS NMR spectra of the Pt-exchanged zeolite Y (HY30, CBV760, Zeolyst Int.), of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively.

FIG. 4 shows the $^{29}$Si MAS NMR spectra of the the Pt-exchanged HY30, of the mesoporized zeolite Y before steaming (HYA), the mesoporized zeolite Y after steaming (HYA-st), the ammonia-treated non-steamed (HYA-NH3) and ammonia-treated steamed (HYA-st-NH3) samples respectively. All spectra show overlapped peaks between −115 and −90 ppm, corresponding to the Si coordinated to one to two Al atoms. The spectra of HY30, HYA and HYA-st are similar, whereas after the treatment with ammonia, the peaks at higher ppm-values increase. This indicates the increase of the relative amount of Si(1Al) and probably also Si(2Al) species pointing out the reconstruction of the zeolitic structure.

Temperature-programmed Desorption of Ammonia TPD-NH$_3$

HY30 showed 0.36 mmol NH$_3$/g. After the desilication (HYA), the amount of acid sites decreased to 0.33 mmol NH$_3$/g. The steaming caused a slight increase in the overall acidity to 0.38 mmol NH$_3$/g. By treating HYA and HYA-st in the presence of gaseous ammonia, the overall acidity of HYA increased to 0.46 and that of HYA-st remained at 0.38 mmol NH$_3$/g.

Transmission and Scanning Electron Microscopy

Example 5

Catalysis—Hydrocracking of Squalane

The samples HY30, HYA, HYA-st, HYA-NH3 and HYA-st-NH3 containing 0.5 wt % Pt were catalytically tested in hydrocracking of squalane (Alfa Aesar, 98.8%). The tests were performed using plug-flow reactors at following operating conditions:
H$_2$ pressure: 20 barg
Temperature: 180-300° C.
WHSV: 3 h$^{-1}$
H$_2$/squalane ratio: 4 mol/mol.

The tests were performed using 1 mL of catalyst (sieved to 120-160 μm), activated at 450° C. (1° C./min) for 4 h in a flow of hydrogen.

FIG. 5 shows the plots of conversion vs. temperature for all samples.

FIG. 6 shows the product distribution plots (weight percentage vs. C-cuts) at 75% conversion based on the data obtained by simulated distillation of the products obtained at different temperatures.

The invention claimed is:

1. A process for preparing a catalyst comprising a mesoporized zeolite with healed zeolitic structure, including the steps of:
A) preparation of a protonic mesoporized zeolite, which contains at least one network of micropores and at least one network of mesopores, and
B) treatment of the protonic mesoporized zeolite obtained in step A) in a gas phase containing a source of ammonia to re-insert extra-framework zeolite Al atoms in octahedral coordination and Al atoms in pentahedral coordination into framework position where Al atoms are in tetrahedral coordination and obtaining a catalyst containing less extra-framework of zeolite Al atoms than the zeolite prepared during step A), thus obtaining a mesoporized zeolite with healed zeolitic structure.

2. The process according to claim 1, wherein the step A) includes the steps of:
a) suspending a parent zeolite as starting material or a composite material comprising the parent zeolite in a basic pH aqueous solution comprising at least one strong base and/or an inorganic or organic weak base, at a concentration ranging from 0.001 to 2 M, at room temperature, with magnetic or mechanical stirring,
b) neutralizing the medium by addition of at least one acid, at a concentration ranging from 0.005 to 2 M, at room temperature, with stirring,
c) separating the zeolite obtained from the liquid and optionally washing it with a solvent,
d) optionally drying the washed zeolite,
e) optionally performing at least one ion exchange treatment of the zeolite from step c) or of the optionally dried zeolite from step d);
f) optionally washing the zeolite,
g) calcining the zeolite obtained, and
h) recovering the protonic mesoporized zeolite.

3. The process according to claim 2, wherein the parent zeolite or a composite material comprising the parent zeolite as starting material has an atomic Si/Al ratio within the zeolite framework between 10 and 50.

4. The process according to claim 2, wherein, in step a), the basic pH solution/ zeolite weight ratio is in the range of 4 to 100.

5. The process according to claim 2, wherein, in step e), a ion exchange solution/mesoporized zeolite weight ratio may range from 3 to 75.

6. The process according to claim 1, wherein the volume percentage of the ammonia source is between 1 and 50 vol %.

7. The process according to claim 1, wherein the treatment according to step B) takes place in the temperature range between 15 and 600° C.

8. The process according to claim 1, including an extrusion step and/or a modification step of the final mesoporized zeolite catalyst (step B)) or of the protonic mesoporized zeolite (step A)) with metals, said metals being chosen from compounds of group VIII, from group VIB and mixture thereof, followed by a calcination step.

9. The process according to claim 2, including an extrusion step applied after step A) using the protonic mesoporized zeolite and before step B), followed by step B) and then by a subsequent modification step with metals, said metals being chosen from compounds of group VIII, from group VIB and mixture thereof, followed by a calcination step.

10. The process according to claim 8, wherein metals from Group VIB are chosen from the group consisting of Cr, Mo and W and metals from Group VIII are chosen from the group consisting of Fe, Ru, Os, Co, Rh, Jr, Ni, Pd, and Pt.

11. The process according to claim 1, wherein after the step A) and before the step B), said process includes a treatment step of the protonic mesoporized zeolite with water vapour.

12. The process according to claim 2, wherein the strong base is selected from the group consisting of NaOH and KOH, and the inorganic or organic weak base is selected from the group consisting of sodium carbonate, sodium citrate and tetraalkyl ammonium hydroxide.

13. The process according to claim 6, wherein the volume percentage of the ammonia source is between 3 and 40 vol %.

14. The process according to claim 6, wherein the volume percentage of the ammonia source is between 5 and 30 vol %.

15. The process according to claim 7, wherein the treatment according to step B) takes place in the temperature range between 20 and 350° C.

\* \* \* \* \*